United States Patent
Liu

(10) Patent No.: US 10,514,431 B2
(45) Date of Patent: Dec. 24, 2019

(54) METHOD AND APPARATUS FOR MAGNETIC RESONANCE IMAGING WITH RF NOISE

(71) Applicant: KONINKLIJKE PHILIPS N.V., Eindhoven (NL)

(72) Inventor: Yong Liu, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 44 days.

(21) Appl. No.: 15/569,789

(22) PCT Filed: Apr. 15, 2016

(86) PCT No.: PCT/EP2016/058302
§ 371 (c)(1),
(2) Date: Oct. 27, 2017

(87) PCT Pub. No.: WO2016/173861
PCT Pub. Date: Nov. 3, 2016

(65) Prior Publication Data
US 2018/0143272 A1   May 24, 2018

(30) Foreign Application Priority Data

Apr. 30, 2015   (WO) ............... PCT/CN2015/077989
Aug. 13, 2015   (WO) ............... PCT/CN2015/086849
Sep. 25, 2015   (EP) .................................... 15186938

(51) Int. Cl.
*G01V 3/00*       (2006.01)
*G01R 33/36*      (2006.01)
(Continued)

(52) U.S. Cl.
CPC ........... *G01R 33/36* (2013.01); *G01R 33/565* (2013.01); *G01R 33/5608* (2013.01); *A61B 5/055* (2013.01)

(58) Field of Classification Search
CPC .................................................. G01R 33/4818
(Continued)

(56) References Cited

U.S. PATENT DOCUMENTS 4,665,368 A    4/1987   Sugiyama et al.
7,279,893 B1   10/2007  Marinelli et al.
(Continued)

FOREIGN PATENT DOCUMENTS

JP    63272336 A     11/1988
WO    2013016639 A1   1/2013
WO    2014167561 A2  10/2014

OTHER PUBLICATIONS

Campbell et al "A Semi-automatic K-Space Dispiking Algorithm for the Removal of Striping Artefacts in MR Images" Proc. of the Intl. Soc. for Magn, Reson. in Med. vol. 20 (2012) p. 2443.

*Primary Examiner* — Louis M Arana

(57) ABSTRACT

Embodiment of the present invention provides a method for cancelling environment noise of a magnetic resonance image (MRI) system that includes a receive antenna. The method comprises acquiring magnetic resonance (MR) data including a noise RF ingredient via the receive antenna, acquiring noise RF data indicative of the environment noise of the MRI system, calculating a compensation factor based on the noise RF data and a part of the MR data limited to a peripheral portion of k-space storing the MR data, estimating the noise RF ingredient of the MR data as a multiplication of the noise RF data and the calculated compensation factor, and generating corrected MR data by subtracting the estimated noise RF ingredient from the MR data.

20 Claims, 7 Drawing Sheets

(51) Int. Cl.
*G01R 33/56* (2006.01)
*G01R 33/565* (2006.01)
*A61B 5/055* (2006.01)

(58) Field of Classification Search
USPC .......................................... 324/309, 322, 318
See application file for complete search history.

(56) References Cited

U.S. PATENT DOCUMENTS

| | | |
|---|---|---|
| 7,486,982 B2 | 2/2009 | Branch et al. |
| 8,970,217 B1 | 3/2015 | Kadin |
| 2004/0164739 A1 | 8/2004 | Peterson et al. |
| 2008/0048658 A1 | 2/2008 | Huskek et al. |
| 2008/0315879 A1 | 12/2008 | Saha |
| 2013/0300413 A1 | 11/2013 | Hwang et al. |
| 2013/0300417 A1 | 11/2013 | Malaney et al. |
| 2014/0070810 A1 | 3/2014 | Robert et al. |
| 2014/0091791 A1 | 4/2014 | Bulumulla et al. |
| 2014/0155732 A1 | 6/2014 | Patz et al. |
| 2017/0108569 A1* | 4/2017 | Harvey .................. G01R 33/36 |
| 2018/0143280 A1* | 5/2018 | Dyvorne ............... G01R 33/445 |
| 2018/0292480 A1* | 10/2018 | Brunner ................ G01R 33/24 |

* cited by examiner

METHOD AND APPARATUS FOR MAGNETIC RESONANCE IMAGING WITH RF NOISE

CROSS REFERENCE TO RELATED APPLICATIONS

This application is a U.S. national phase application of International Application No. PCT/EP2016/058302, filed on Apr. 15, 2016, which claims the benefit of CN Application Serial Nos. PCT/CN2015/077989 filed Apr. 30, 2015 and PCT/CN2015/086849 filed Aug. 13, 2015 and EP Application Serial No. 15186938.5 filed Sep. 25, 2015 and are incorporated herein by reference.

FIELD OF THE INVENTION

The invention relates to magnetic resonance imaging, in particular to magnetic resonance imaging in the presence of spurious RF signals.

BACKGROUND OF THE INVENTION

A large static magnetic field is used by Magnetic Resonance Imaging (MRI) scanners to align the nuclear spins of atoms as part of the procedure for producing images within the body of a patient. This large static magnetic field is referred to as the B0 field or the main magnetic field.

During an MRI scan, Radio Frequency (RF) pulses generated by a transmitter coil cause perturbations to the local magnetic field, and RF signals emitted by the nuclear spins are detected by a receiver coil. These RF signals are used to construct the MRI images. These coils can also be referred to as antennas. Further, the transmitter and receiver coils can also be integrated into a single transceiver coil that performs both functions. It is understood that the use of the term transceiver coil also refers to systems where separate transmitter and receiver coils are used. The transmitted RF field is referred to as the B1 field.

However, spurious RF noise during the MRI scan can interfere with the measurement of the RF signals emitted by the nuclear spins. Typically, a large RF cage is built around the magnetic resonance imaging system to eliminate these spurious RF signals. A disadvantage to using such an RF cage is that it uses large amounts of metal such as copper and is expensive to build.

U.S. Pat. No. 7,486,982 B2 discloses a radio-opaque holder in combination with radio-opaque magnet components to form an RF shield around a patient undergoing an NMR procedure.

JPS63272336A discloses two sets of external radiowave detection coils that are arranged in the vicinity of the MR signal detection coil but substantionally do not perform the reception of the MR signal from the examinee. The effect of the external radiowave is removed by directly subtracting the receiving signal of the external radiowave detection coils from that of the MR signal detection coil. It is understood that the external radiowave detections coils have to be carefully placed relative to the signal detection coil to ensure the effect of noise cancellation. The international application WO2013/016639 discloses an active noise cancellation system in a portable MR system, which calculates a universal complex scaling factor and determines a transfer function between environmental spurious noise and the measured signal from the receiver coil, which is herein incorporated by reference in its entirety.

SUMMARY OF THE INVENTION

It is an object of the invention to provide a cost effective noise cancellation approach with the least possible modification to hardware of magnetic resonance imaging systems on the market. Meanwhile, the noise cancellation approach takes into account temporal and spatial noise evolution to improve the accuracy of correcting imaging magnetic resonance data.

Embodiments of the invention provide a magnetic resonance imaging system, a method, and a computer program product in the independent claims. Embodiments are given in the dependent claims.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa. The contents of the memory and storage may duplicate each other or items depicted as being in one may be stored or copied in the other.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer to indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins by the antenna of a magnetic resonance apparatus during a magnetic resonance imaging scan. Magnetic resonance data is an example of medical image data. A Magnetic Resonance Imaging (MRI) image is defined herein as being the reconstructed two or three dimensional visualization of anatomic data contained within the magnetic resonance imaging data. This visualization can be performed using a computer. Magnetic resonance data may also be referred to as k-space data. K-space is a formalism widely used in magnetic resonance imaging. In MRI physics, k-space is the 2D or 3D Fourier transform of the MR image measured. In practice, K-space often refers to the temporary image space, usually a matrix of complex value, in which data from digitized MR signals are stored during data acquisition.

Embodiments of the present invention provide a method for cancelling environment noise of a magnetic resonance image (MRI) system that includes a receive antenna. The method comprises acquiring magnetic resonance (MR) data including a noise RF ingredient via the receive antenna, acquiring noise RF data indicative of the environment noise of the MRI system, calculating a compensation factor based on the noise RF data and a part of the MR data in a peripheral portion of k-space storing the MR data, estimating the noise RF ingredient of the MR data as a multiplication of the noise RF data and the calculated compensation factor, and generating corrected MR data by subtracting the estimated noise RF ingredient from the MR data. Advantageously, by taking into account the distribution characteristic of the noise RF ingredient in k-space of MR data, the peripheral portion of k-space where the noise RF ingredient dominates is used for compensation factor calculation. As such, the noise cancellation can be achieved with the least possible modification to system hardware and meanwhile the noise is cancelled in a more accurate way.

According to one embodiment of the present invention, the noise RF data is acquired via a sniffer coil positioned outside an imaging volume of the MRI system. Advantageously, the sniffer coil can measure predominantly the environment noise to obtain more accurate noise RF data.

According to one embodiment of the present invention, the sniffer coil is a standard receive antenna positioned outside the imaging volume as the sniffer coil and the noise RF data is acquired via the standard receive antenna simultaneously with acquisition of the MR data via the receive antenna positioned within the imaging volume. Advantageously, a spare standard receive antenna on the niche can be reused as the sniffer coil directly, which saves the cost and effort of designing a specified sniffer coil dedicated for noise RF data measurement. Moreover, modification to magnetic resonance imaging system to make it compatible with the dedicated sniffer coil is avoided as well. Meanwhile, using the standard receive antenna as the sniffer coil also makes simultaneous acquisition of MR data and noise RF data simpler compared to using the dedicated sniffer coil.

According to one embodiment of the present invention, the receive antenna is formed as a multi-channel coil array, wherein the noise RF data is acquired via a virtual sniffer module implemented by a processor to extract the RF noise data from the MR data acquired via the multi-channel coil array. Advantageously, by extracting the noise RF data from the MR data acquired via the multi-channel coil array, the cost of noise cancellation is further reduced since no hardware is involved.

According to one embodiment of the present invention, the noise RF data from the MR data acquired via the multi-channel coil array is extracted using a statistic algorithm selected from the group consisting of a principle component analysis (PCA) and an independent component analysis (ICA). Advantageously, the statistic algorithm can be executed by a computer program product to save cost.

According to one embodiment of the present invention, calculating the compensating factor further comprises aligning data lines of k-space storing the MR data with data lines of k-space storing the RF noise data, the aligned data lines having the same k value in phase encoding direction, and calculating the compensation factor based on the MR data of data lines near the highest/lowest k values in phase encoding direction of corresponding k-space and the RF noise data of data lines near the highest/lowest k values in phase encoding direction of corresponding k-space, wherein the MR data of data lines near the highest/lowest k values is a multiplication of the compensation factor and the RF noise data of data lines near the highest/lowest k values. Advantageously, the compensation factor can be computed for each aligned phase encoding gradient to consider the temporal evolution of the environment noise in each reception period of the MR data.

According to one embodiment of the present invention, calculating the compensating factor further comprises aligning data lines of k-space storing the MR data with data lines of k-space storing the RF noise data, the aligned data lines having the same k value in phase encoding direction, and calculating the compensation factor based on the MR data near the highest/lowest k values in frequency encoding direction for data lines in center of phase encoding direction of corresponding k-space and the RF noise data near the highest/lowest k values in frequency encoding direction for data lines in center of phase encoding direction of corresponding k-space, wherein the MR data near the highest/lowest k values is a multiplication of the compensation factor and the RF noise data near the highest/lowest k values. Advantageously, the compensation factor can be computed for each aligned phase encoding gradient to consider the temporal evolution of the environment noise in each reception period of the MR data.

According to one embodiment of the present invention, calculating the compensating factor further comprises aligning data lines of k-space storing the MR data with data lines of k-space storing the RF noise data, the aligned data lines having the same k value in phase encoding direction, and calculating the compensation factor based on the MR data near the highest/lowest k values in frequency encoding direction of corresponding k-space and the RF noise data near the highest/lowest k values in frequency encoding direction of corresponding k-space, wherein the MR data near the highest/lowest k values is a multiplication of the compensation factor and the RF noise data near the highest/ lowest k values. Advantageously, the compensation factor can be computed for each aligned phase encoding gradient to consider the temporal evolution of the environment noise in each reception period of the MR data.

Embodiments of the present invention provide a magnetic resonance image system configured to cancel a noise ingredient of MR data acquire via a receive antenna of the MRI. The MRI system comprises a data acquisition module configured to acquire noise RF data indicative of environment noise of the MRI system and the MR data acquired via the receive antenna, a compensation factor calculation module configured to calculate a compensation factor based on the noise RF data and a part of the MR data in a peripheral portion of k-space storing the MR data, a noise estimation module configured to estimate the noise RF ingredient of the MR data as a multiplication of the noise RF data and the calculated compensation factor, and a data correction module configured to generate corrected MR data by subtracting the estimated noise RF ingredient from the MR data. Advantageously, by taking into account the distribution characteristic of the noise RF ingredient in k-space of MR data, the peripheral portion of k-space where the noise RF ingredient dominates is used for compensation factor calculation. As such, the noise cancellation can be achieved with the least possible modification to system hardware and meanwhile the noise is cancelled in a more accurate way.

According to one embodiment of the present invention, the compensation factor is a 1-dimensional complex vector for each channel of the multi-channel coil array and the number of vector elements is equal to the number of phase encoding gradients to correct the imaging magnetic resonance data acquired during each reception period based on different vector elements.

Embodiments of the present invention provide a computer program product comprising machine executable instructions for execution by a processor controlling a magnetic resonance imaging system. Execution of the machine executable instructions causes the processor to: acquire noise RF data indicative of environment noise of the MRI system and the MR data acquired via the receive antenna, calculate a compensation factor based on the noise RF data and a part of the MR data in a peripheral portion of k-space storing the MR data, estimate the noise RF ingredient of the MR data as a multiplication of the noise RF data and the calculated compensation factor, and generate corrected MR data by subtracting the estimated noise RF ingredient from the MR data. Advantageously, by taking into account the distribution characteristic of the noise RF ingredient in k-space of MR data, the peripheral portion of k-space where the noise RF ingredient dominates is used for compensation factor calculation. As such, the noise cancellation can be achieved with the least possible modification to system hardware and meanwhile the noise is cancelled in a more accurate way.

Various aspects and features of the disclosure are described in further detail below. And other objects and advantages of the present invention will become more apparent and will be easily understood with reference to the description made in combination with the accompanying drawings.

DESCRIPTION OF THE DRAWINGS

The present invention will be described and explained hereinafter in more detail in combination with embodiments and with reference to the drawings, wherein.

Figure 1:
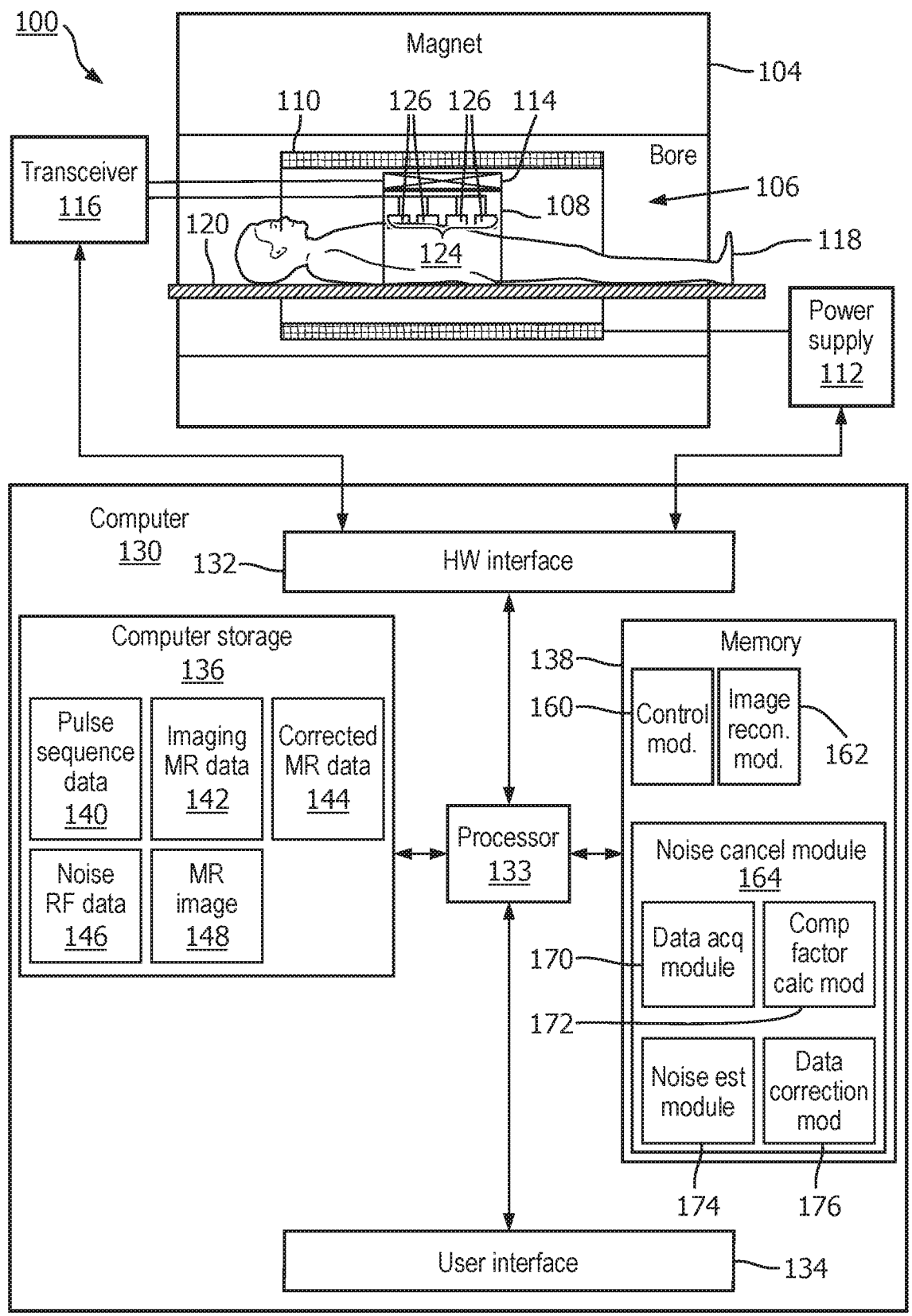
FIG. 1 illustrates a magnetic resonance imaging system according to one embodiment of the present invention.

The same reference signs in the figures indicate similar or corresponding feature and/or functionality.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes.

DETAILED DESCRIPTION OF THE EMBODIMENT

Like numbered elements in these figures are either equivalent elements or perform the same function. Elements which have been discussed previously will not necessarily be discussed in later figures if the function is equivalent.

FIG. 1 shows an example of a magnetic resonance imaging system 100. The magnetic resonance imaging system 100 comprises a magnet 104. The magnet 104 is a superconducting cylindrical type magnet 104 with a bore 106 through it. The use of different types of magnets is also possible, for instance, it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 106 of the cylindrical magnet 104 there is an imaging zone 108 where the magnetic field is strong and uniform enough to perform magnetic resonance imaging.

Within the bore 106 of the magnet there is also a set of magnetic field gradient coils 110 which is used for acquisition of magnetic resonance data to spatially encode magnetic spins within the imaging zone 108 of the magnet 104. The magnetic field gradient coils 110 are connected to a magnetic field gradient coil power supply 112. The magnetic field gradient coils 110 are intended to be representative. Typically magnetic field gradient coils 110 contain three separate sets of coils for spatially encoding in three orthogonal spatial directions. A magnetic field gradient power supply 112 supplies current to the magnetic field gradient coils. The current supplied to the magnetic field gradient coils 110 is controlled as a function of time and may be ramped or pulsed. A subject support 120 supports a subject 118 within the imaging zone 108.

Within the bore 106 of the magnet 104 is a body coil 114. The body coil 114 may be a QBC. The body coil 114 is shown as being connected to a transceiver 116. In some embodiments, body coil 114 may also be connected to a whole body coil radio frequency amplifier and/or receiver, however this is not shown in this example. If both a transmitter and a receiver 116 are connected to the whole body coil 114, a means for switching between the transmit and receive mode may be provided. For example a circuit with a pin diode may be used to select the transmit or receive mode.

The transceiver 116 is shown as being connected to a receive antenna 124. In this example, the receive antenna 124 is formed as a multi-channel coil array comprising multiple coil loops 126.

The transceiver 116 and the magnetic field gradient coil power supply 112 are shown as being connected to a hardware interface 132 of a computer 130. The computer 130 is further shown as containing a processor 133 which is operable for executing the machine-readable instructions. The computer 130 is further shown as comprising a user interface 134, computer storage 136 and computer memory 138 which are all accessible and connected to the processor 133.

The computer storage 136 is shown as containing pulse sequence data 140. The computer storage 136 is further shown as containing imaging magnetic resonance data 142, corrected magnetic resonance data 144 and noise RF data 146. The imaging magnetic resonance data 142 is acquired using the pulse sequence data 140 via the receive antenna 114, 124 and includes a RF noise ingredient from the environmental spurious noise that is added to the desired magnetic resonance data from the subject 118, e.g., a patient. The noise RF data 146 is indicative of environmental spurious noise of the magnetic resonance imaging system 100. The corrected magnetic resonance data 144 has had the RF noise ingredient removed. The computer storage 136 is further shown as containing a magnetic resonance image 148 that has been reconstructed from the corrected imaging magnetic resonance data 144. As aforementioned, the receive antenna 124 may include multiple coil loops 126. In this instance, the imaging magnetic resonance data 142 includes multiple subsets of channel magnetic resonance data, each subset corresponding to one of the multiple coil loops 126. Accordingly, each subset of channel magnetic resonance data have corresponding channel RF noise ingredient and corrected channel magnetic resonance data 144. For the purpose of illustration, the following noise cancellation algorithm is described mainly with reference to the imaging magnetic resonance data 142 of one channel.

The computer memory 138 is shown as containing a control module 160. The control module contains computer-executable code which enables the processor 133 to control the operation and function of the magnetic resonance imaging system 100. The computer storage 138 is shown as optionally containing an image reconstruction module 162 which enables the processor 133 to reconstruct magnetic resonance images 148 from the corrected magnetic resonance data 144. The computer memory 138 is further shown as containing a noise cancellation module 164. The noise cancellation module 164 contains computer-executable code which enables the processor 133 to perform the noise removal from the imaging magnetic resonance data 142 to generate the corrected imaging magnetic resonance data 144. The example control module, image reconsturciton module and noise concellation module of the illustrated example of FIG. 1 are implemented by a processor executing instructions, but they could alternatively be implemented by an ASIC, DSP, FPGA, or other circuitry.

In one embodiment, the noise cancellation module 164 further comprises a data acquisition module 170, a compensation factor calculation module 172, a noise estimation module 174 and a data correction module 176. Similarly, the data acquisition module 170, the compensation factor calculation module 172, the noise estimation module 174 and the data correction module 176 of the illustrated example of FIG. 1 are implemented by the processor 133 executing instructions, but they could alternatively be implemented by an ASIC, DSP, FPGA, or other circuitry. The data acquisition module 170 contains computer-executable code which enables the processor 133 to read the imaging magnetic resonance data 142 and the noise RF data 146 stored in the computer storage 136. As the imaging magnetic resonance data 142 is inclusive of the desired magnetic resonance signal from the subject 118 and the RF noise ingredient from the environment spurious noise, it can be given by equation (1)

$$S_{RX} = N_{EX} + S_{MR} \qquad (1)$$

where $S_{RX}$ represents the imaging magnetic resonance data 142 acquired via the receive antenna 124, $N_{EX}$ represents the RF noise ingredient from the environment noise, and $S_{MR}$ represents the desired MR signal from the subject 118. As aforementioned, the noise RF data 146 is indicative of environmental noise of the magnetic resonance imaging system 100. By considering the amplitude and phase difference of the environmental noise at different positions of the scanning room, the noise RF data 146 can be transferred to the RF noise ingredient by multiplying a compensation factor according to equation (2)

$$N_{Ex} = N_R *$$

where $N_R$ represents noise RF data 146. The compensation factor is a complex ratio and thus the equation (2) can also be expressed as $$N_{EX} = N_R * A e^{-jt}$$

where the magnitude A of complex ratio represents the path loss of the environment noise to reach a specific receive channel 126 in a multi-channel receive antenna 124, represents a carrier frequency of the environment noise, and time delay t represents the different time of arrival (TOA) of the environment noise reaching different coil loops 126 at their positions in a multi-channel receiving coil 124.

In addition, as aforementioned, the receive antenna 124 is formed as a multi-channel coil array comprising multiple coil loops 126. Each antenna channel generates its own k-space after magnet resonance signal reception. Usually, the environment noise propagates along various paths to reach each antenna channel at different times. As a result, the captured noise ingredients by each antenna channel vary in strength. Beside the uneven strength, those noise ingredients in k-space of each antenna channel are shifted by time delays as a result of various time of arrival. Advantageously, the noise cancellation approach as discussed in relation to equations (1), (2) and (3), can be applied to each channel data k-space to calculate a 1-dimensional complex compensation vector for the corresponding antenna channel. As such, the strength and phase variation across the antenna channels is considered in environment noise cancellation. Considering the above, as long as the compensation factor for a specific channel can be obtained, the RF noise ingredient added to the desired magnetic resonance data can be estimated according to equation (2). In one embodiment, the compensation factor calculation module 172 contains computer-executable code which enables the processor 133 to implement the algorithm as described below to calculate the compensation factor.

Figures 2A, 2B:
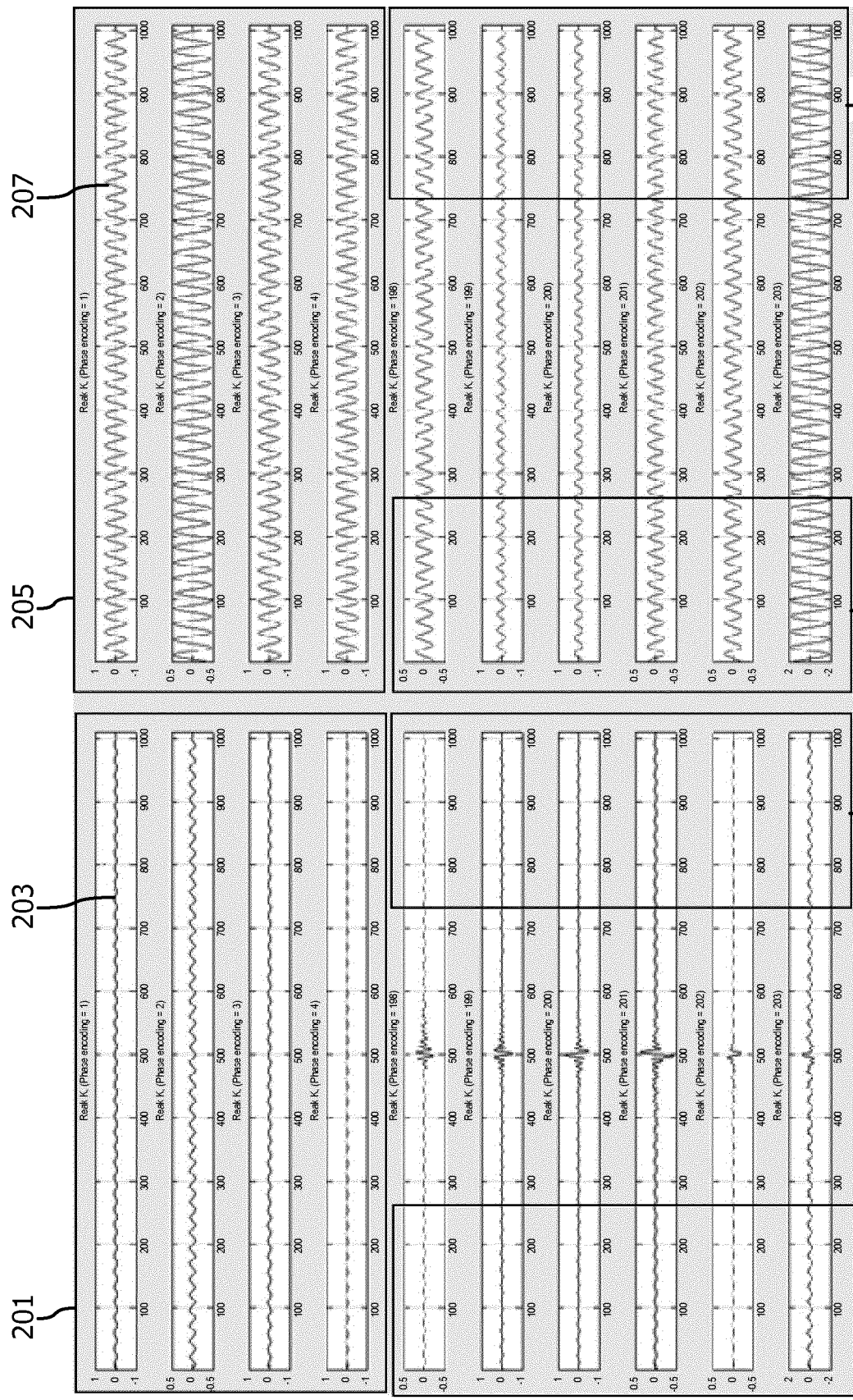
FIG. 2a illustrates peripheral portions of a k-space representation that contains the image data and RF noise data obtained from one magnetic resonance scan according to one embodiment of the present invention.
FIG. 2b illustrates peripheral portions of a k-space representation that contains the RF noise data only according to one embodiment of the present invention.

With reference to FIG. 2a and FIG. 2b, a k-space representation FIG. 2a of imaging magnetic resonance data 142 is compared with a k-space representation FIG. 2b of noise RF data 146. In the example of FIG. 2a and FIG. 2b, both k-spaces have the size of 1000 frequency encoding gradients (k values) by 400 phase encoding gradients (k values). For the purpose of clarity and conciseness, only the top edge and center portions of the k-spaces are illustrated herein. Since the noise RF data 146 is sampled simultaneously with sampling of the imaging magnetic resonance data 142, the data lines of the imaging magnetic resonance data k-space of FIG. 2a is aligned with the data lines of the noise RF data k-space of FIG. 2b. For each of the phase encoding gradients, data samples in data lines of FIG. 2a can be modeled as $S_{RX}$, which is a function of data samples in corresponding data lines of FIG. 2b, e.g., modeled as $N_R$, according to equations 1) and 2).

Referring to FIG. 2a, an edge portion 201, e.g., the portion containing data lines with phase encoding gradients (k values) from 1 to 4, stores fairly weak magnetic resonance signals due to the strong dephase effect of spin caused by the highest phase encoding gradient field. The sinusoid like waves 203 present at the edge portion 201 mainly represents the RF noise ingredient from the environment noise. Referring to FIG. 2b, an edge portion 205, e.g., the portion containing data lines captured in the same of phase encoding gradients from 1 to 4, shows clear and strong sinusoid waves 207 which represent the baseband data of noise RF data 146.

Since the edge portion 201 of the imaging magnetic resonance data k-space is dominated by the RF noise ingredient, the equations 1) and 2) can be modified to obtain equation 4) by assuming that on data lines in edge portion 201 of the imaging magnetic resonance data k-space, the desired magnetic resonance signal from the subject 118 is zero, $$S_{RX\_N} = N_{R\_N}*$$

where $S_{RX\_N}$ represents data samples on data line N in edge portion 201 of the imaging magnetic resonance data k space, $N_{R\_N}$ represents data samples on data line N in edge portion 205 of the noise RF data k space, and represents the compensation factor for the data line N in the edge portion 201 of the MR data k space. A solution for is to solve a least squares minimization problem to minimize M $$M = \Sigma |S_{R\_N} - N_{R\_N}*|^2$$

For data lines in the center portion of k-space, e.g., phase encoding gradient around 200 in FIG. 2a and FIG. 2b, the imaging magnetic resonance signals at the echo center of those data lines are so strong that the RF noise ingredient is not in a dominant position. Accordingly, equation 4) is not readily applicable to data lines in the center portion of k-space. However, with reference to FIG. 2a, the RF noise ingredient still dominates the data lines around k-space center at the front and rear portions 210 of those data lines due to the strong dephase effect when the echo center is far away. As such, the equation 4) can be modified to $$S'_{RX\_N} = N'_{R\_N}*$$

by only using the data samples in the front and rear portions 210 and 220 of data lines around the imaging magnetic resonance data k-space center and noise RF data k-space center, respectively. That is to say, $S'_{RX\_N}$ represents data samples at the front and rear portions 210 of data lines around imaging magnetic resonance data k-space center and $N'_{R\_N}$ represents data samples at the front and rear portions 220 of data line around noise RF data k-space center. Similarly, a solution for the data line N around imaging magnetic resonance data k-space center is to solve the least squares minimization problem to minimize M'

$$M' = \Sigma |S'_{RX\_N} - N'_{R\_N}*|^2 \qquad (7)$$

In summary, compensation factor calculation module 172 first selects a peripheral portion (201, 210) of k-space storing the imaging magnetic resonance data 142 where the RF noise ingredient dominates, e.g., the data lines in the top and bottom edge of k-space and the front and rear portions of data lines around k-space center. Then, the compensation factor for each data line N is calculated according to equations (4) and (5) when the data line N is at the top and bottom edge of k-space and according to equations (6) and (7) when the data line N is around the k-space center.

As aforementioned, k-space is the 2D or 3D Fourier transform of the MR image measured. In practice, K-space often refers to the temporary image space, in which data from digitized MR signals are stored in the form of 2D or 3D complex matrix with nice symmetry property. The center of a 2D k-space, i.e. the middle k value in both frequency and phase encoding direction, has the largest MR signal samples, because the spin precession remains in the in-phase state. The peripheral portion of matrix, e.g, the largest/lowest k-value regions in either frequency of phase encoding direction of 2 2D k-space has the relatively low MR signal samples, because of the dephase state of spin precession. For example, 10% or less of the total of phase encoding lines with the largest/lowest k-values symmetrically distributed across the center phase encoding line, or 80% or less of the total of frequency encoding lines with the largest/lowest k-values symmetrically distributed across the center frequency encoding lines, can be referred to as peripheral portions in a 2D k-space. In some instances, due to delay in MR signal reception or intended pulse design, the k-space center is shifted forward or backwared with respect to the geometry center of the matrix, causing said 80% or less of the total of frequency encoding lines to be unevenly distributed. In both circumstances, the peripheral portion of k-space used for noise cancellation can be determined through multiple trials to obtain the most preferable compensation factor which results in the best image quality. For a 3D K-space, the $3^{rd}$ dimension is phase encoded. Each 2D K-space slice also has a frequency and phase encoding direction, which is the case for both MR data K-space and noise RF data K-space. Then, each slice of k-space will be treated as an individual channel during the calculation of compensation factors.

With the calculated compensation factor for each data line, the noise estimation module 174 can estimate the noise ingredient $N_{EX}$ added to the desired MR signal $S_{MR}$ according to equation (2). With the estimated noise ingredient $N_{EX}$, the data correction module 176 can obtain the desired MR signal $S_{MR}$ from the subject 118 by subtracting the estimated noise ingredient $N_{EX}$ from the imaging magnetic resonance data 142 acquired via the receive antenna 124, thereby realizing the RF noise cancellation.

Advantageously, by considering the distribution characteristic of imaging magnetic resonance raw data in k-space, more specifically, the RF noise ingredient dominating the peripheral portion of the k-space, the peripheral portion of the k-space dominated by the RF noise ingredient is selected for compensation factor calculation. Moreover, a compensation factor for each data line is calculated individually by taking into account of the RF noise distribution on each data line. As such, a compensation factor vector is obtained where each vector element represents the compensation factor for the data line of phase encoding gradient N. Such an approach can capture environmental noise evolution for each repetition time TR to obtain different compensation factor for each phase encoding gradient, which significantly enhances the temporal resolution of environment noise cancellation.

Figure 3A:
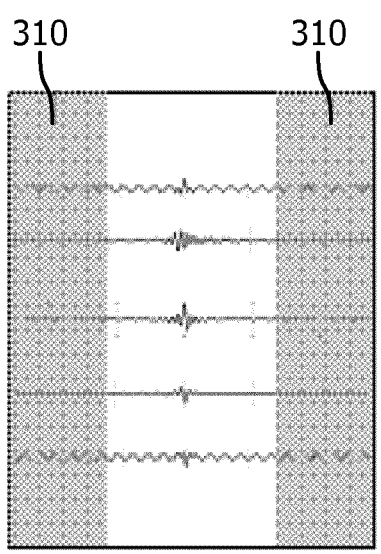
FIG. 3a illustrates peripheral portions of a k-space representation that contains the image data and RF noise data obtained from one magnetic resonance scan according to another embodiment of the present invention.
Figure 3B:
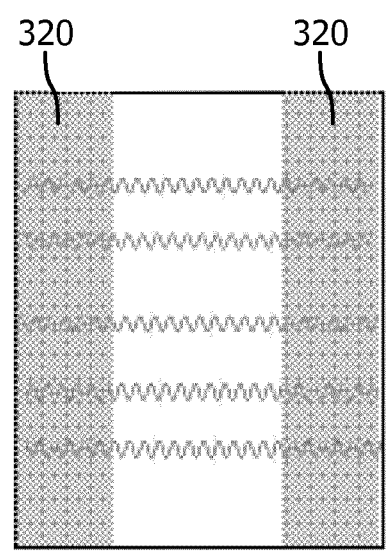
FIG. 3b illustrates peripheral portions of k-space representation that contains the RF noise data only according to another embodiment of the present invention.

Alternatively, as a tradeoff between precision and speed of environmental noise cancellation, data samples in the front and rear portions 310 of data lines throughout the whole imaging magnetic resonance data k-space of FIG. 3a and data samples in the front and rear portions 320 of data lines throughout the whole noise RF data k-space of FIG. 3b are selected for compensating factor calculation according to equations (6) and (7).

Moreover, it is understood that to realize real-time noise cancellation, the noise RF data 146 needs to be acquired simultaneously with the imaging magnetic resonance data 142. Embodiments below will describe in more details how simultaneous reception of the noise RF data 146 and imaging magnetic resonance data 142 is achieved.

Figure 4:
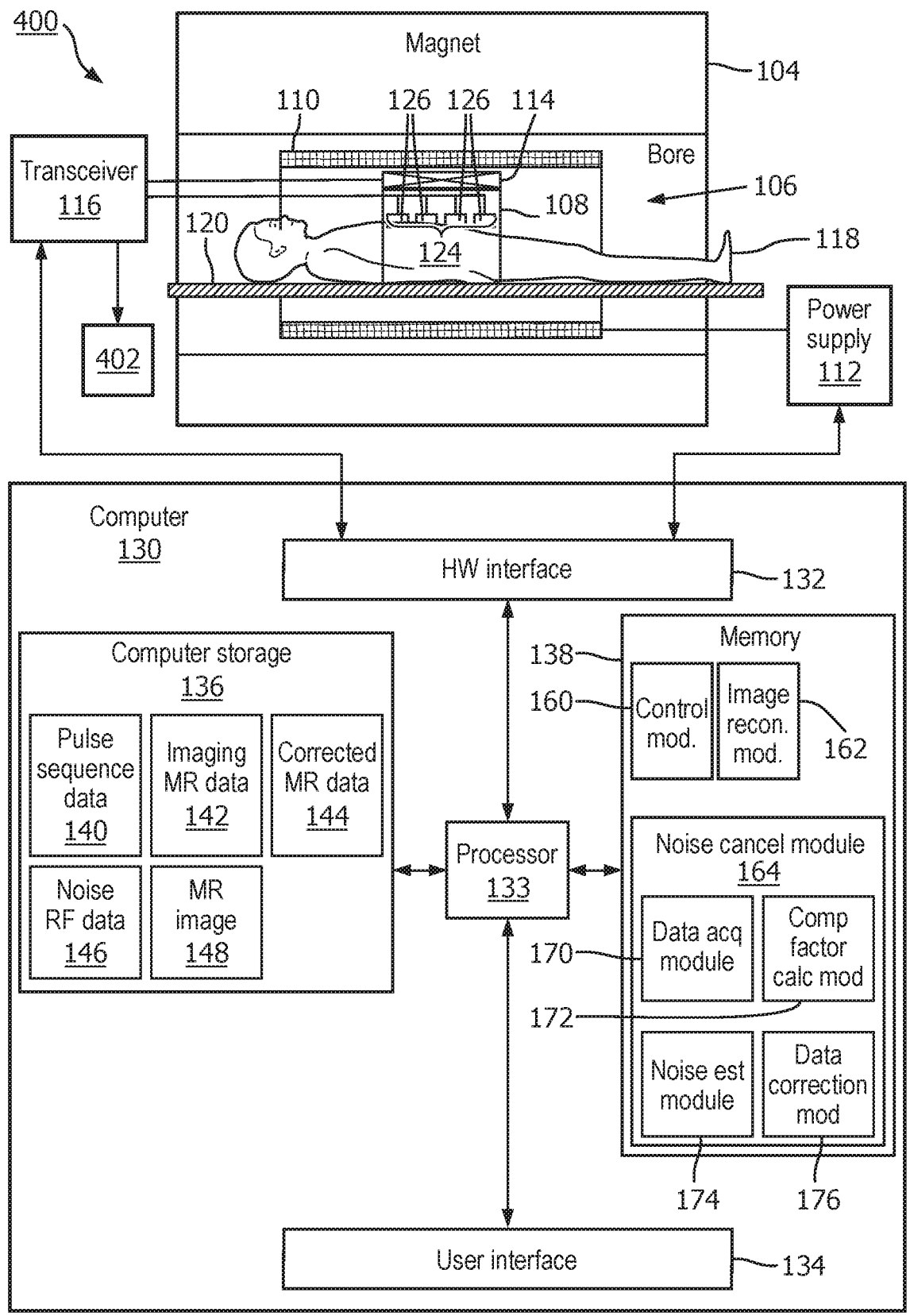
FIG. 4 illustrates a magnetic resonance imaging system according to another embodiment of the present invention.

With reference to FIG. 4, the magnetic resonance imaging system 400 is shown as having a sniffer coil 402 located outside the bore 106 of the magnetic resonance imaging system 400. The sniffer coil 402 is placed away from the imaging zone 108. The acquisition of the noise RF data 146 is in synchronicity with the acquisition of imaging magnetic resonance data 142, only that the signal that the sniffer coil 402 measures would be predominantly noise RF data 146 as opposed to the coil 114 or 124 which measures noise plus magnetic resonance signals 142 from the subject 118.

The transceiver 116 is shown as being further connected to the sniffer coil 402. The transceiver 116 is a multi-channel transceiver. In some embodiments the transceiver 116 may be split into several different units. However, it may be beneficial to use additional channels of the transceiver 116 for the sniffer coil 402 as the signals acquired will be handled in the same way as data acquired using the antennas 114, 124.

Figure 5:
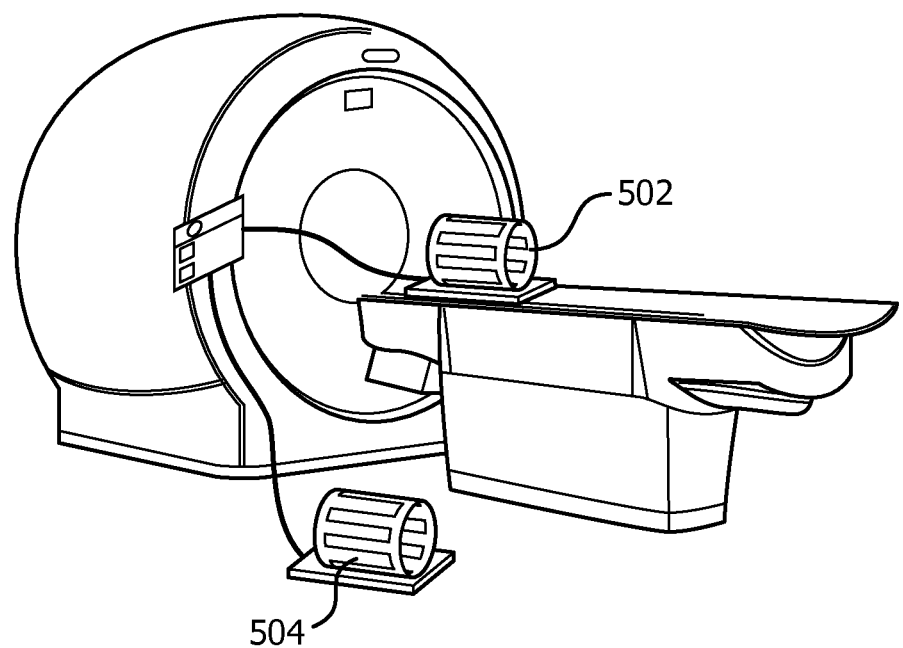
FIG. 5 illustrates an example of the sniffer coil in FIG. 4 according to one embodiment of the present invention.

Generally, the magnetic resonance imaging system 400 will be equipped with a lot of standard receive coils, e.g., head coils, spine coils, wrist coil, etc. When a certain standard receive coil is placed within the imaging zone 108 to detect the imaging magnetic resonance signals, spare standard receive coils are on the niche in an idle state. Advantageously, with current noise cancellation approach, such spare standard receive coils can be reused as the sniffer coil 402 to be placed outside the imaging zone 108 to predominately measure the environment noise. In the example of FIG. 5, one head coil 502 is slid into the imaging zone 108 to detect the imaging magnetic resonance signal, while another spare head coil 504 is placed on the floor of the scanning room which is remote from the imaging zone 108 to only measure the environment noise. Since the head coil 504 placed outside the imaging zone 108 is also a standard receive coil, the magnetic resonance imaging system 400 will handle it in the same way as the head coil 502. As such, no hardware modification is necessitated for magnetic resonance imaging system 400 to realize the acquisition of environment noise in synchronicity with the acquisition of imaging magnetic resonance data, nor a dedicated sniffer coil is required. Put it another way, by reusing a standard receive coil as the sniffer coil, a conventional magnetic resonance imaging system can be easily adapted to perform the noise cancellation function when the environment noise is present The noise cancellation module 164 is needed in this noise cancelling process as well.

Figure 6:
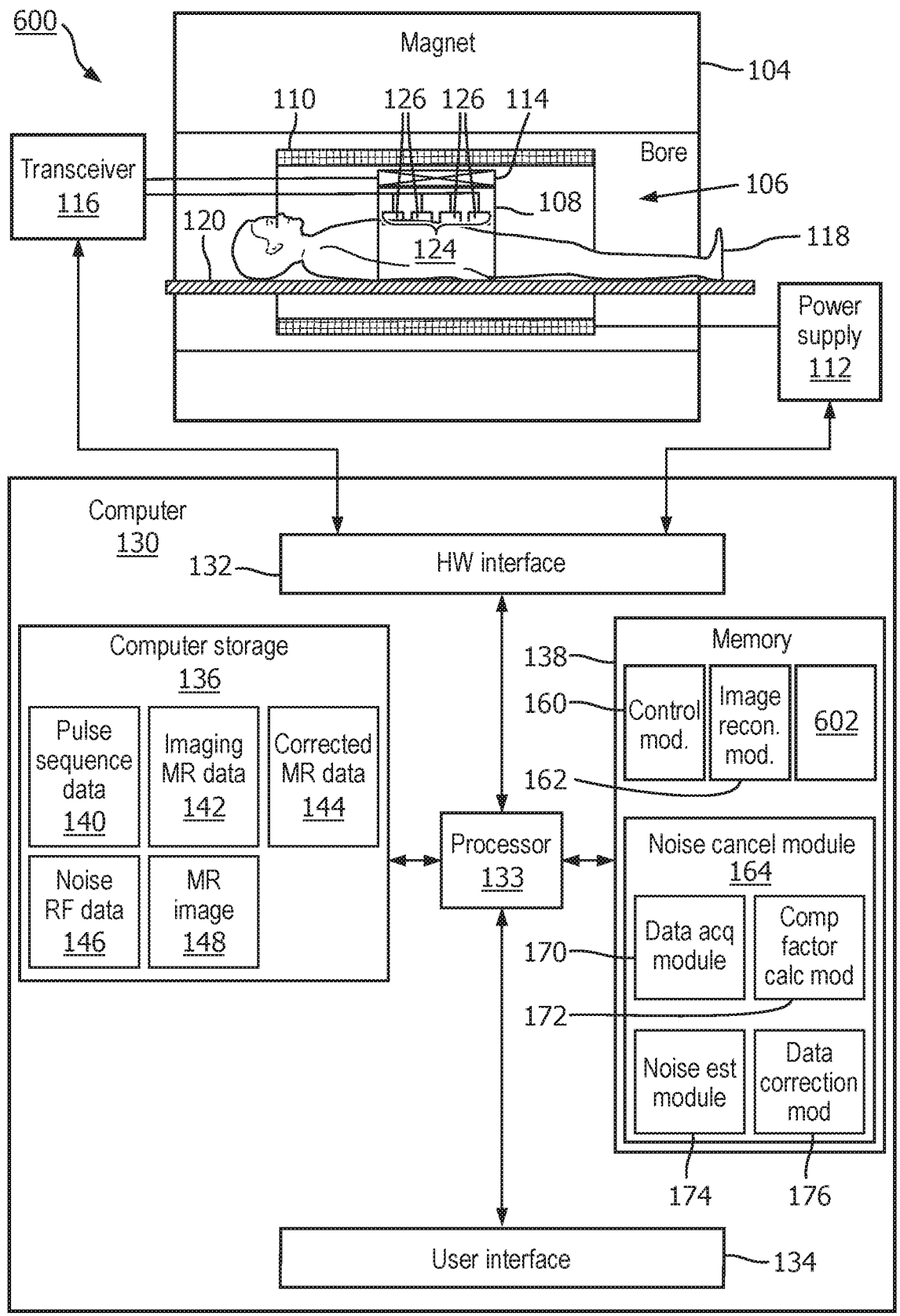
FIG. 6 illustrates a magnetic resonance imaging system according to yet another embodiment of the present invention.

Alternatively, for the receive antenna 124 with multiple coil loops 126, the noise ingredients inclusive in the multi-channel raw data are not only statistically closely correlated but also linearly correlated, which allows usage of a statistic method to extract the noise RF data 146 indicative of the environment noise from the multi-channel raw data. As shown in FIG. 6, such statistic method is implemented by a virtual sniffer module 602 which contains computer-executable code to enable the processor 133 to extract the noise RF data 146 from the multi-channel magnetic resonance dataset 142 and generate the reference noise RF data 146 for de-nosing procedure illustrated in FIG. 2a/FIG. 2b and FIG. 3a/FIG. 3b.

One exemplary statistic method for noise RF data extraction is principle component analysis (PCA). The joint data analysis on two or more channel data will identify the RF noise distribution with time and within K-space frame as a unique eigen vector and extracted to form the noise RF data 146. The MR signals, which are distributed among channel data unlike the RF noise, will be also identified as a different eigen vector and extracted to form the imaging magnetic resonance data 142. The following steps for noise cancellation are the same as above, which will not be described again for conciseness.

Alternatively, other statistic method for noise RF data extraction can also be used, such as the independent component analysis (ICA). Advantageously, by using the virtual sniffer module 602, no hardware cost is involved and therefore the noise cancellation is realized in a more cost-effective way.

It should be understood by the skilled in the art that it is not necessary to use the imaging MR data from all antenna channels to extract the noise RF data.

Figure 7:
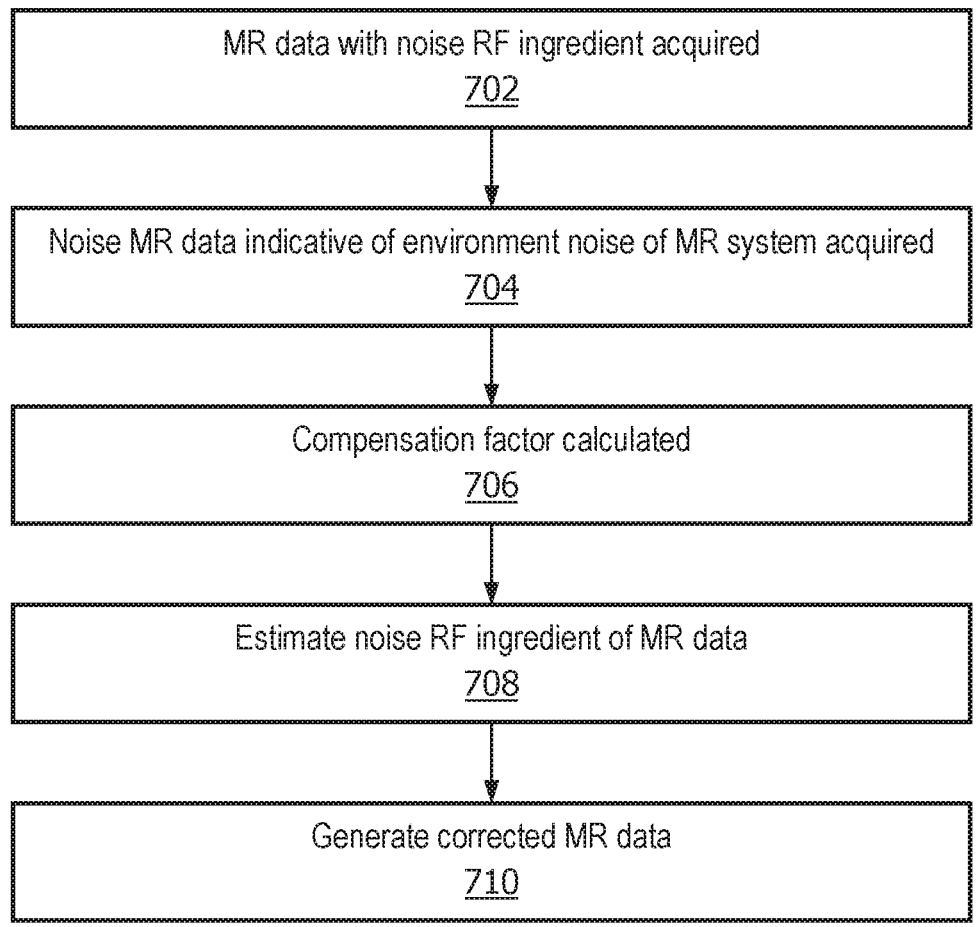
FIG. 7 shows a flow chart of a method for cancelling environment noise of a magnetic resonance image (MRI) system according to one embodiment of the present invention.

FIG. 7 illustrates a flow chart 700 of a method for cancelling environment noise in a magnetic resonance image system according to one embodiment of the present invention.

At step 702, magnetic resonance data inclusive of noise RF ingredient is acquired via a receive antenna. In the embodiment of FIG. 1, the imaging magnetic resonance data 142 which includes noise RF ingredient from the environment noise is acquired via the receive antenna 124.

At step 704, noise RF data indicative of the environment noise of the MRI system is acquired. In the embodiment of FIG. 4, the noise RF data is acquired via the sniffer coil 402. In the embodiment of FIG. 6, the noise RF data is acquired by extracting it from the multi-channel magnetic resonance data 142 via a virtual sniffer module 602.

At step 706, a compensation factor is calculated based on the noise RF data and a part of the MR data in a peripheral portion of k-space storing the magnetic resonance data. In the embodiment of FIG. 2a, the peripheral portions 201 and 210 of the k-space storing the imaging magnetic resonance data 142 are selected for compensation factor calculation according to equations 5) and 7). In the embodiment of FIG. 3a, the peripheral portion 310 of the k-space storing the imaging magnetic resonance data 142 is selected for compensation factor calculation according to equation 7).

At step 708, the noise RF ingredient of the magnetic resonance data is estimated as a multiplication of the noise RF data and the calculated compensation factor. In the embodiment of FIG. 1, the noise estimation module 174 estimates the noise RF ingredient of the imaging magnetic resonance data 142 according to equation 2).

At step 710, the corrected magnetic resonance data is generated by subtracting the estimated noise RF ingredient from the magnetic resonance data. In the embodiment of FIG. 1, the data correction module 176 generates the corrected magnetic resonance data 144 by subtracting the estimated noise RF ingredient from the imaging magnetic resonance data 142 according to equation 1).

Please note that, the apparatus and the method according to the present invention should not be limited only to the apparatus and method mentioned above. It will be apparent to those skilled in the art that the various aspects of the invention claimed may be practiced in other examples that depart from these specific details.

Furthermore, the mere fact that certain measures are recited in mutually different dependent claims does not indicate that a combination of these measures cannot be used to advantage.

It should be noted that the above-mentioned embodiments illustrate rather than limit the invention and that those skilled in the art would be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. In the product claims enumerating several units, several of these units can be embodied by one and the same item of software and/or hardware. The usage of the words first, second and third, et cetera, does not indicate any ordering. These words are to be interpreted as names.

The invention claimed is:

1. A method for cancelling environment noise of a magnetic resonance image (MRI) system that includes a receive antenna, the method comprising:
   acquiring magnetic resonance (MR) data in k-space via the receive antenna, wherein the MR data includes a noise RF ingredient;
   acquiring noise RF data in k-space and indicative of the environment noise of the MRI system, the method characterized in further comprising:
   calculating a compensation factor transferring the noise RF data to the noise ingredient of the MR data based on the noise RF data and a part of the MR data limited to a peripheral portion of k-space storing the MR data;
   estimating the noise RF ingredient of the MR data as a multiplication of the noise RF data and the calculated compensation factor; and
   generating corrected MR data by subtracting the estimated noise RF ingredient from the MR data.

2. The method of claim 1, wherein calculating the compensation factor further comprising:
   aligning data lines of k-space storing the MR data with data lines of k-space storing the RF noise data, wherein the aligned data lines have the same k value in phase encoding direction; and
   calculating the compensation factor based on the MR data of data lines near the highest/lowest k values in phase encoding direction of corresponding k-space and the RF noise data of data lines near the highest/lowest k values in phase encoding direction of corresponding k-space, wherein the MR data of data lines near the highest/lowest k values is a multiplication of the compensation factor and the RF noise data of data lines near the highest/lowest k values.

3. The method of claim 1, wherein calculating the compensation factor further comprising:
   aligning data lines of k-space storing the MR data with data lines of k-space storing the RF noise data, wherein the aligned data lines have the same k value in phase encoding direction; and
   calculating the compensation factor based on the MR data near the highest/lowest k values in frequency encoding direction for data lines in center of phase encoding direction of corresponding k-space and the RF noise data near the highest/lowest k values in frequency encoding direction for data lines in center of phase encoding direction of corresponding k-space, wherein the MR data near the highest/lowest k values is a multiplication of the compensation factor and the RF noise data near the highest/lowest k values.

4. The method of claim 1, wherein calculating the compensation factor further comprising:
   aligning data lines of k-space storing the MR data with data lines of k-space storing the RF noise data, wherein the aligned data lines have the same k value in phase encoding direction; and
   calculating the compensation factor based on the MR data near the highest/lowest k values in frequency encoding direction of corresponding k-space and the RF noise data near the highest/lowest k values in frequency encoding direction of corresponding k-space, wherein the MR data near the highest/lowest k values is a multiplication of the compensation factor and the RF noise data near the highest/lowest k values.

5. The method of claim 1, wherein the noise RF data is acquired via a sniffer coil positioned outside an imaging volume of the MRI system.

6. The method of claim 5, wherein the sniffer coil is a secondary receive antenna positioned outside the imaging volume as the sniffer coil, and wherein the noise RF data is acquired via the secondary receive antenna simultaneously with acquisition of the MR data via the receive antenna positioned within the imaging volume.

7. The method of claim 1, wherein the receive antenna is formed as a multi-channel coil array, and wherein the noise RF data is acquired via a virtual sniffer module implemented by a processor to extract the RF noise data from the MR data acquired via the multi-channel coil array.

8. The method of claim 7, further comprising:
   extracting the noise RF data from the MR data acquired via the multi-channel coil array using a statistic algorithm selected from the group consisting of a principle component analysis (PCA) and an independent component analysis (ICA).

9. A magnetic resonance image system configured to cancel a noise ingredient of MR data in k-space and acquired via a receive antenna of the MRI system, the MRI system comprising:
   a data acquisition module configured to acquire noise RF data in k-space and indicative of environment noise of the MRI system and the MR data acquired via the receive antenna;
   a compensation factor calculation module configured to calculate a compensation factor transferring the noise RF data to the noise ingredient of the MR data based on the noise RF data and a part of the MR data limited to a peripheral portion of k-space storing the MR data;

a noise estimation module configured to estimate the noise RF ingredient of the MR data as a multiplication of the noise RF data and the calculated compensation factor;

a data correction module configured to generate corrected MR data by subtracting the estimated noise RF ingredient from the MR data.

10. The system of claim 9, wherein the noise RF data is acquired via a sniffer coil arranged outside an imaging volume of the MRI system.

11. The system of claim 9, wherein a secondary receive antenna arranged outside the imaging volume is used as the sniffer coil, and wherein the noise RF data is detected via the secondary receive antenna (504) simultaneously with acquisition of the MR data via the receive antenna arranged within the imaging volume.

12. The system of claim 9, wherein the receive antenna is formed as a multi-channel coil array, and wherein the noise RF data is acquired via a virtual sniffer module implemented by a processor to extract the RF noise data from the MR data acquired via the multi-channel coil array.

13. The system of claim 12, wherein the virtual sniffer module uses a statistic algorithm selected from the group consisting of a principle component analysis (PCA) and an independent component analysis (ICA) to extract the noise RF data from the MR data acquired via the multi-channel coil array.

14. The system of claim 12, wherein the compensation factor is a 1-dimensional complex vector for each channel of the multi-channel coil array and the number of vector elements is equal to the number of phase encoding gradients to correct the imaging magnetic resonance data acquired during each reception period based on different vector elements.

15. A non-transitory computer executable media comprising machine executable instructions for execution by a processor controlling a magnetic resonance imaging system that includes a receive antenna, wherein execution of the machine executable instructions causes the processor to:
   acquire noise RF data in k-space and indicative of environment noise of the MRI system and the MR data in k-space and acquired via the receive antenna;
   calculate a compensation factor transferring the noise RF data to the noise ingredient of the MR data based on the noise RF data and a part of the MR data limited to a peripheral portion of k-space storing the MR data;
   estimate the noise RF ingredient of the MR data as a multiplication of the noise RF data and the calculated compensation factor; and
   generate corrected MR data by subtracting the estimated noise RF ingredient from the MR data.

16. The non-transitory computer executable media of claim 15, wherein calculating the compensation factor further comprising:
   aligning data lines of k-space storing the MR data with data lines of k-space storing the RF noise data, wherein the aligned data lines have the same k value in phase encoding direction; and
   calculating the compensation factor based on the MR data of data lines near the highest/lowest k values in phase encoding direction of corresponding k-space and the RF noise data of data lines near the highest/lowest k values in phase encoding direction of corresponding k-space, wherein the MR data of data lines near the highest/lowest k values is a multiplication of the compensation factor and the RF noise data of data lines near the highest/lowest k values.

17. The non-transitory computer executable media of claim 15, wherein calculating the compensation factor further comprising:
   aligning data lines of k-space storing the MR data with data lines of k-space storing the RF noise data, wherein the aligned data lines have the same k value in phase encoding direction; and
   calculating the compensation factor based on the MR data near the highest/lowest k values in frequency encoding direction for data lines in center of phase encoding direction of corresponding k-space and the RF noise data near the highest/lowest k values in frequency encoding direction for data lines in center of phase encoding direction of corresponding k-space, wherein the MR data near the highest/lowest k values is a multiplication of the compensation factor and the RF noise data near the highest/lowest k values.

18. The non-transitory computer executable media of claim 15, wherein calculating the compensation factor further comprising:
   aligning data lines of k-space storing the MR data with data lines of k-space storing the RF noise data, wherein the aligned data lines have the same k value in phase encoding direction; and
   calculating the compensation factor based on the MR data near the highest/lowest k values in frequency encoding direction of corresponding k-space and the RF noise data near the highest/lowest k values in frequency encoding direction of corresponding k-space, wherein the MR data near the highest/lowest k values is a multiplication of the compensation factor and the RF noise data near the highest/lowest k values.

19. The non-transitory computer executable media of claim 15, wherein the noise RF data is acquired via a sniffer coil positioned outside an imaging volume of the MRI system.

20. The non-transitory computer executable media of claim 19, wherein the sniffer coil is a secondary receive antenna positioned outside the imaging volume as the sniffer coil, and wherein the noise RF data is acquired via the secondary receive antenna simultaneously with acquisition of the MR data via the receive antenna positioned within the imaging volume.

* * * * *